United States Patent [19]
Jeffs et al.

[11] Patent Number: 5,711,446
[45] Date of Patent: Jan. 27, 1998

[54] CRYOGENIC FREEZING VIAL

[75] Inventors: David H. Jeffs, Draper; Stephen Mackert, Sandy, both of Utah

[73] Assignee: Sorenson BioScience, Inc., Salt Lake City, Utah

[21] Appl. No.: 585,627

[22] Filed: Jan. 16, 1996

[51] Int. Cl.[6] ............................................ B65D 21/02
[52] U.S. Cl. .................... 220/23.83; 220/522; 220/506
[58] Field of Search ............................... 220/521, 522, 220/212, 410, 408, 506, 505, 23.83, 420, 425, 446, 468, 469; 215/228

[56] References Cited

U.S. PATENT DOCUMENTS

| | | | |
|---|---|---|---|
| 1,140,414 | 5/1912 | Steel | 220/204 |
| 2,044,093 | 11/1934 | Mills | 220/447 |
| 2,252,750 | 8/1941 | Basch | 374/16 |
| 2,495,942 | 1/1950 | Nosik | 220/522 |
| 2,615,448 | 10/1952 | Fields | 220/522 |
| 3,247,302 | 4/1966 | Lewis | 264/245 |
| 3,275,180 | 9/1966 | Optner et al. | 220/445 |
| 3,807,955 | 4/1974 | Note, Jr. et al. | 436/177 |
| 3,819,081 | 6/1974 | Runte | 220/17 |
| 4,299,100 | 11/1981 | Crisman et al. | 62/457 |
| 4,471,911 | 9/1984 | Hengesbach | 220/410 |
| 4,756,446 | 7/1988 | Gen et al. | 220/410 |
| 4,850,496 | 7/1989 | Rudell et al. | 220/425 |
| 4,865,014 | 9/1989 | Nelson | 220/410 |
| 5,036,998 | 8/1991 | Dunn | 220/469 |
| 5,502,981 | 4/1996 | Sullivan | 220/522 |

*Primary Examiner*—Stephen J. Castellano
*Attorney, Agent, or Firm*—Thorpe, North & Western

[57] ABSTRACT

A cryogenic freezing vial. The vial includes a hollow sample container having exterior threads seated inside a hollow outer container having interior threads. The two containers define a surrounding volume there between which operates as a thermal barrier to resist temperature change within the sample container. A cap having a tubular wall extending outwardly from a continuous capping surface includes threads formed on both of the opposing sides of the tubular wall. The inner threaded side of the tubular wall can be screwed onto the hollow sample container, and then the outer threaded side of the tubular wall can be screwed into the hollow outer container. In such manner the cap is disposed in simultaneous threaded engagement between the two containers to intercouple and seal the containers from their surrounding environment.

13 Claims, 2 Drawing Sheets

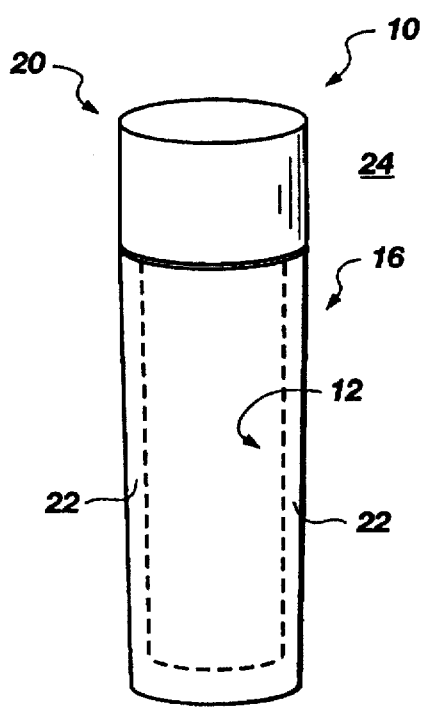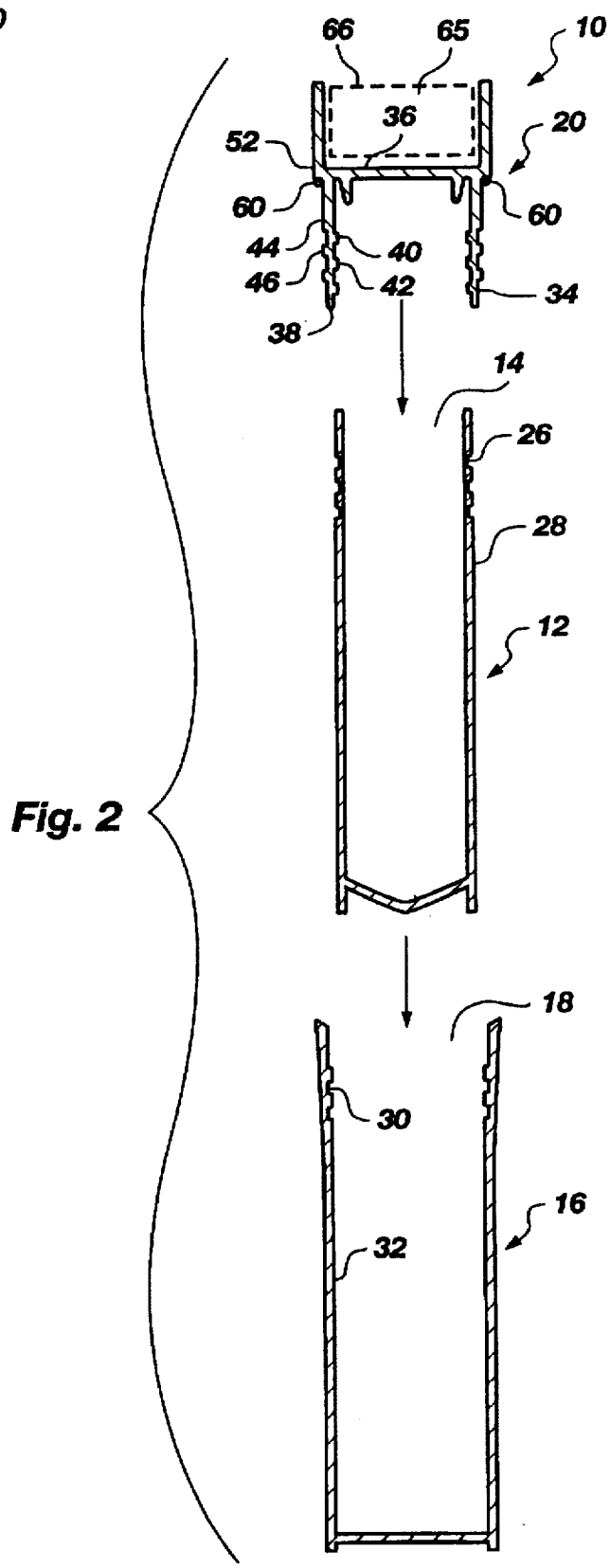

CRYOGENIC FREEZING VIAL

BACKGROUND OF THE INVENTION

1. The Field of the Invention

The present invention relates generally to specimen containers. More particularly, it concerns a cryogenic freezing vial for encapsulating biological specimens at very low temperatures.

2. The Background Art

Cryogenic freezing vials are known in the art for storing live cells from semen, body tissues, and other biological samples. The vials are suspended in freezers and liquid nitrogen or any suitable freezing medium, and are thereby maintained at extremely low temperatures for the purpose of preserving the cells. One of the problems encountered is that the cell viability decreases if the cell temperature is raised or lowered too rapidly, such as during initial freezing in the liquid nitrogen or during thawing upon removal from the liquid nitrogen. It is known to freeze the vials in separate stages to avoid large temperature change rates, such as by placing the vials in separate freezer units of intermediate lower temperatures prior to placing them into liquid nitrogen.

The conventional vials and methods of controlling their temperature rate are characterized by a number of disadvantages. The staged temperature control method requires additional time, labor and expense involved in transferring the vials, and poses additional risk to the samples each time the vials are moved. Further, although the caps on the vials are sealed, after extended periods of storage the liquid nitrogen eventually seeps past the seal and into the vial to contaminate the sample. The unwanted seepage is aided in part by a vacuum effect produced within the vial by the freezing action of the liquid nitrogen. In addition, prior art cryogenic vials will sometimes explode into fragments during the thawing process with such a force that some of fragments are known to penetrate surrounding sheetrock walls.

OBJECTS AND SUMMARY OF THE INVENTION

It is therefore an object of the present invention to provide a vial which slows down the rate of temperature change within the vial.

It is another object of the invention to provide such a vial which has an increased capacity to seal a contained volume within the vial from environment surrounding the vial.

It is a further object of the invention to provide such a vial which is less likely to explode during thawing thereof.

The above objects and others not specifically recited are realized in a specific illustrative embodiment of a cryogenic freezing vial. The vial includes a hollow sample container having exterior threads seated inside a hollow outer container having interior threads. The two containers define a surrounding volume there between which operates as a thermal barrier to resist temperature change within the sample container. A cap having a tubular wall extending outwardly from a continuous capping surface includes threads formed on both of the opposing sides of the tubular wall. The inner threaded side of the tubular wall can be screwed onto the hollow sample container, and then the outer threaded side of the tubular wall can be screwed into the hollow outer container. In such manner the cap is disposed in simultaneous threaded engagement between the two containers to intercouple and seal the containers from their surrounding environment.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which:

FIG. 1 is a perspective view of a cryogenic freezing vial made in accordance with the principles of the present invention;

FIG. 2 is an exploded side, cross-sectional view of the vial of FIG. 1;

DETAILED DESCRIPTION OF PRESENTLY PREFERRED EMBODIMENTS

Figure 3:
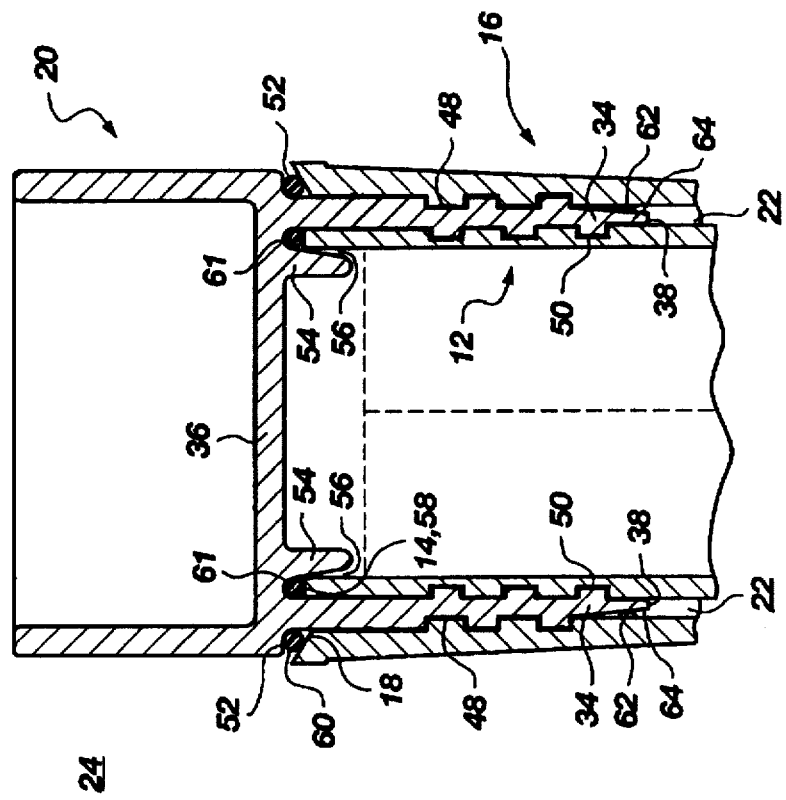
FIG. 3 is an enlarged, fragmented view of the vial of FIG. 2 in an assembled configuration.

Referring now to FIGS. 1–2, there is shown a cryogenic freezing vial, generally designated at 10, made in accordance with the present invention. The vial 10 includes a hollow inner container, designated generally at 12 and having an open end 14. The inner container 12 is configured for receiving a sample therein such as a biological specimen. A hollow outer container, designated generally at 16, includes an open end 18 and is configured for receiving the inner container 12 therein as shown.

A cap, designated generally at 20, operates as a one-piece unitary interconnecting means in that it is removably attachable to both the inner and outer containers 12 and 16 for (i) removably securing the inner container 12 within the outer container 16 in a fixed position such that the containers define a surrounding volume 22 therebetween which surrounds at least a portion of the inner container 12, and (ii) substantially closing off the open ends 14 and 18 of the inner and outer containers 12 and 16 from communication with surrounding environment 24 of the vial 10 such that the inner container 12 is also substantially closed off from communication with the surrounding volume 22.

The containers 12 and 16 are preferably tubular. The inner container 12 includes threads 26 formed upon an outer surface 28 thereof. The outer container 16 includes threads 30 formed upon an inner surface 32 thereof. The cap 20 includes a tubular wall 34 extending outwardly form a continuous capping surface 36 to a terminal rim 38. The tubular wall 34 includes an inner surface 40 having threads 42 which are screwably engageable with the threads 26 of the inner container 12. The tubular wall 34 further includes an opposing outer surface 44 having threads 46 which are screwably engageable with the threads 30 of the outer container 16. The inner surface 40 of the cap 20 can be screwed onto the threads 26 of the inner container 12, and then the outer surface 44 can be screwed into the threads 30 of the outer container 16. In such manner the cap 20 is disposed in simultaneous threaded engagement with both the inner and outer containers 12 and 16 so as to be positioned simultaneously over the open ends 14 and 18 of the containers, as shown by inspection of FIGS. 1–2. The capping surface 36 and the tubular wall 34 cooperatively close off the open ends 14 and 18 of the containers 12 and 16.

Figure 4:
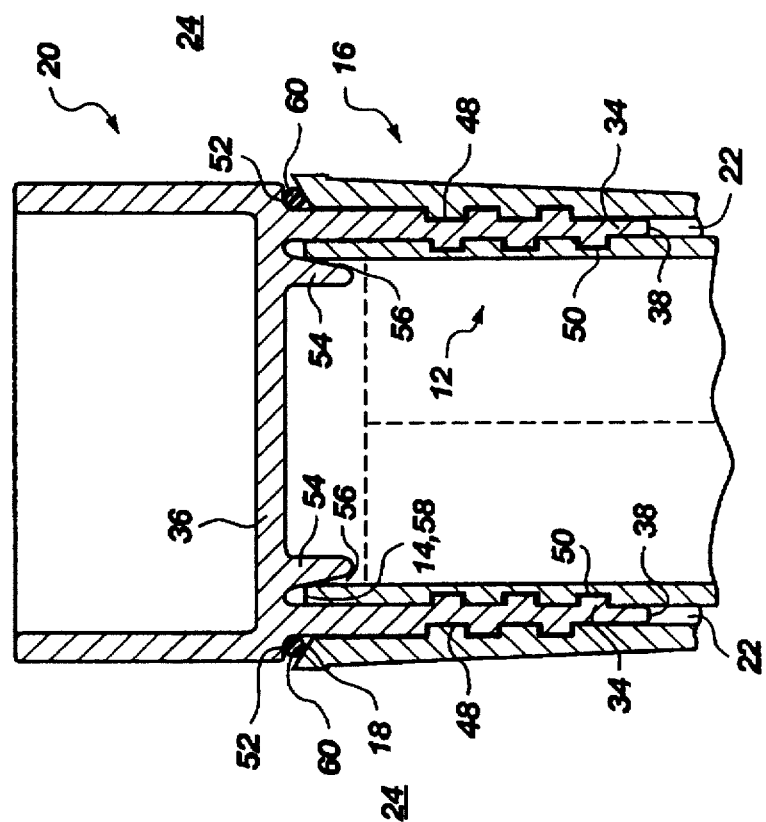
FIG. 4 is a fragmented view of an alternative embodiment of the vial of FIG. 3.

As shown most clearly in FIGS. 3–4, the containers 12 and 16 and the cap member 20 cooperatively define a substantially closed tortuous path between the surrounding environment 24 and the open end 14 of the inner container 12. The tortuous path extends from the environment 24 into the open end 18 of the outer container 16 and along threaded engagement 48 between the outer container 16 and the tubular wall 34 of the cap member 20, into the surrounding volume 22 and around the terminal rim 38 of the tubular wall 34, along threaded engagement 50 between the tubular wall 34 and the inner container 12, around the open end 14 of the inner container 12 and into the inner container 12.

In operation, a sample (not shown) such as a biological specimen is placed into the inner container 12. The vial 10 is assembled as in FIG. 2 by screwing the cap 20 onto the inner container 12 to advance the open end 14 of the inner container 12 toward the capping surface 36. The cap 20 is also screwed into the outer container 16 to advance the open end 18 of the outer container 16 toward the capping surface 36 such that the vial 10 appears in its assembled configuration as shown in FIGS. 1 and 3–4. The vial 10 is then suspended in liquid nitrogen (not shown) to reduce the temperature of the sample contained within the inner container 12. Preferably, the open end 18 of the outer container 16 is advanceable into contact against the cap 20 when the tubular wall 34 of the cap 20 is being screwed onto the outer container 16. It is also preferred that the open end 14 of the inner container 12 be advanceable into contact against the cap 20 when the tubular wall 34 of the cap 20 is being screwed onto the inner container 12. The capping surface 36 preferably includes an outer lip 52 for abutting against the open end 18 of the outer container 16.

The substantially closed tortuous path described above between the surrounding environment 24 and the inner container 12 inhibits communication between the environment 24 and the inner container 12. Such communication can be inhibited further by provision of either or both of (i) inner sealing means for establishing an inner seal between the open end 14 of the inner container 12 and the cap 20, and (ii) outer sealing means for establishing an outer seal between the open end 18 of the outer container 16 and the cap 20 to thereby seal the surrounding volume 22 from communication with the surrounding environment 24.

The inner sealing means preferably comprises an annular rib 54 extending outwardly from the capping surface 36 in concentric, substantially co-axial orientation with the tubular wall 34 of the cap 20. The rib 54 defines an annular channel 56 between the rib 54 and the tubular wall 34, such that when the cap 20 is screwed onto the inner container 12 to advance the open end 14 toward the capping surface 36, the open end 14 becomes sealably engaged within the annular channel 56. The sealed engagement is produced when a terminal rim 58 of the inner container 12 becomes bi-compressed between the annular rib 54 and the tubular wall 34 of the cap 20, as shown in FIG. 3, when the cap 20 is screwed firmly onto the inner container 12 to advance the open end 14 toward the capping surface 36. In the alternative, the terminal rim 58 can be configured and dimensioned as shown by the phantom-line extension thereof in FIG. 3 such that the sealed engagement is produced by tri-compression of the terminal rim 58 against the capping surface 36, the annular rib 54 and the tubular wall 34 of the cap 20 when the cap 20 is screwed onto the inner container 12.

An alternative embodiment of the inner sealing means is illustrated by non-limiting example in FIG. 4. Either in lieu of or in addition to the bi-compression or tri-compression described above, a second resilient sealing ring 61 is configured for placement between the capping surface 36 and the terminal rim 58 of the inner container 12. The second ring 61 may be provided either in lieu of or in addition to the annular rib 54, the second 61 circumscribing the rib 54 in the latter case so as to reside within the annular channel 56. When the cap 20 is screwed onto the inner container 12 to advance the open end 14 toward the capping surface 36, the second ring 61 becomes sealably sandwiched between the terminal rim 58 and the capping surface 36.

The outer sealing means preferably comprises a resilient ring 60 configured for placement between the open end 18 of the outer container 16 and the cap 20 so as to circumscribe the tubular wall 34 of the cap 20. When the cap 20 is screwed onto the outer container 16 to advance the open end 18 toward the capping surface 36, the resilient ring 60 becomes sealably sandwiched between said open end 18 and said cap 20. Most preferably, the ring 60 is sealably sandwiched between the outer lip 52 of the capping surface 36 and the open end 18 of the outer container 16. The resilient ring 60 is preferably made of silicone.

The tortuous path is thus a series of sealing points which include the resilient ring 60 (if present), multiple sealing points along the threaded engagement 48, and sealing engagement of rim 58 within annular channel 56 (if present).

Referring now to FIG. 4, additional sealing means are also in accordance with the principles of the present invention. For example and by non-limiting illustration only, a third resilient sealing ring 62 can be disposed around the inner surface 32 of the outer container 16 so as to extend radially inward therefrom. The third sealing ring 62 and the tubular wall 34 of the cap 20 are cooperatively configured and dimensioned to be engageable against each other when the tubular wall 34 is screwed into the outer container 16 to produce the threaded engagement 48 to thereby establish a seal between the outer container and the tubular wall of the cap. The third resilient ring 62 is preferably made of silicone and formed as an integral, fixedly attached extension of the inner surface 32 of the outer container 16. The third ring 62 is of such a small size that screwable advancement of the tubular wall 34 into the outer container 16 is not precluded upon initial engagement between the third ring 62 of the tubular wall 34. The tubular wall 34 can be tapered at 64 near its terminal rim 38 as shown in FIG. 4 to avoid contact between the tubular wall 34 and the third ring 62 until precisely at the location desired to further enable the tubular wall 34 to be screwed completely into the outer container 16.

A preferred method for making the vial 10 includes the steps of:

(a) forming a hollow inner container having an open end and being configured for receiving a sample therein through the open end;

(b) forming a hollow outer container having an open end and being configured for receiving the inner container therein; and (c) forming one-piece unitary interconnecting means removably attachable to both the inner and outer container for (1) removably securing the inner container within the outer container in a fixed, seated position such that the containers define a surrounding volume therebetween which surrounds at least a portion of the inner container, and (2) closing off the open ends of the inner and outer containers from communication with surrounding environment of the vial such that the inner container is also closed off from communication with the surrounding volume.

Applicant notes that the prior art cryogenic vials fail to solve adequately the problem of liquid nitrogen leaking into the vial and contaminating the sample. When the vial is suspended in liquid nitrogen at very low temperatures, a vacuum or suction effect is produced within the vial which operates upon the seal. The seal is often compromised when the vial is stored in the liquid nitrogen for an extended period of time, such that the vacuum effect produced within the vial operates to draw the liquid nitrogen into the vial to contaminate the sample therein.

The principles of the present invention operate to reduce the vacuum force as it might become applied to the surrounding environment 24 of the vial 10, to thereby reduce the risk of drawing the nitrogen (or any other part of the surrounding environment 24) into the sample. The vacuum force produced within the vial by the low temperatures is proportional to the magnitude of the contained volume within the vial. As such, the contained volume within the inner container 12 could be described as a vacuum-producing volume when the temperature is lowered. Similarly, the surrounding volume 22 would also be a vacuum-producing volume. The surrounding volume 22 is preferably substantially smaller in volume than the contained volume within the inner container 12, and therefore produces a much lower vacuum force than does the contained volume within the inner container 12.

Further, inspection of FIGS. 3–4 reveals that the volume within the inner container 12, the surrounding volume 22, and the surrounding environment 24 are positioned in series, with the surrounding environment 24 being sealably "sandwiched" in residence between the volume within the inner container 12 and the surrounding environment 24. More specifically, communication between the volume contained within the inner container 12 and the surrounding environment 24 must pass through (i) the inner sealing engagement between the terminal rim 58 and the rib 54, (ii) the surrounding volume 22, and (iii) the outer sealing engagement produced by the resilient ring 60. Therefore, any vacuum force which might become applied to the outer seal established by the first sealing ring 60 is substantially limited in magnitude by the much smaller volume of the surrounding volume 22 and not the larger contained volume within the inner container 12. Even if both the inner seal between rim 58 and rib 54 and the outer seal of the ring 60 were broken such that vacuum force produced within the inner container 12 is communicable with the surrounding environment 24, any vacuum communication with the environment 24 would still be at least limited by, even if not completely determined by, the volume of the surrounding volume 22 because of the tortuous nature of the interconnecting path between the volume contained within the inner container 12 and the surrounding volume 22.

In accordance with the principles of the present invention as the above description, a preferred method for minimizing vacuum force applied by a contained volume to an environment surrounding the contained volume includes the steps of:

(a) encapsulating a first contained, vacuum-producing volume within an outer container means to form a container system wherein said first contained volume and the outer container means define a second contained, vacuum-producing volume therebetween which surrounds at least a portion of the first contained volume, said second contained volume being substantially smaller in volume than said first contained volume, wherein any vacuum force produced by the first volume or second volume is proportional to the volume of the volume producing it;

(b) sealing the first volume with secondary sealing means;

(c) sealing the second volume from the container system's surrounding environment with primary sealing means;

(d) forming an interconnecting path within the container system to interconnect the secondary and primary sealing means such that any of said vacuum force which might happen to escape into communication with the container system's surrounding environment is thereby directed past the primary sealing means so that any such escaping vacuum force is substantially limited in magnitude by the volume of the second contained volume.

It will be appreciated that the surrounding volume 22 operates as a thermal barrier to aid in solving the problem of temperature changing too quickly and thereby killing or otherwise impairing the biological specimen contained within the vial 10. Accordingly, a preferred method for preserving a biological sample residing within a contained volume which is subject to freezing and thawing action includes the following step:

(a) encapsulating a first container within an outer container means to form a container system wherein said first container and the outer container means define a volume therebetween which surrounds at least a portion of a first contained volume within the first container to thereby provide a thermal barrier around said first contained volume for slowing any heat transfer which may occur between the first contained around and environment surrounding the container system, said first container being configured for encapsulating the biological sample therein.

The surrounding volume 22 also operates as a barrier to inhibit explosion in the vial 10. The problem of the prior art cryogenic vials exploding during the thawing process after removal from liquid nitrogen is inhibited by the double-wall nature of the vial 10.

The wall thickness of the inner and outer containers 12 and 16 is preferably $^{30}/_{1000}$ of an inch, as is the preferably thickness of the surrounding volume 22. Of course, any variation in one or more of the thicknesses of the walls of the containers 12 and 16 and the volume 22 is in accordance with the principles of the present invention.

It is to be understood that the invention as described above may be expressed in a number of structurally-varying embodiments. For example, the containers 12 and 16 and the cap 20 need not be provided with threads, but might instead be cooperatively configured so as to produce some kind of interference fit of the cap 20 onto both of the containers 12 and 16, such as a tongue-and-groove fit or any other suitable fit. As such, the containers 12 and 16 and the cap 20 need not be tubular but may embody any cross-sectional shape such as square, triangular, trapezoidal and so forth. The annular channel 54 might in such cases be replaced by a channel having a square shape or some other shape, any such channel being generically referred to herein by the phrase "endless channel".

It is also to be understood that the open ends 14 and 18 of the containers 12 and 16 need not be engaged, or even engageable, against any part of the cap 20, although such is preferred. Accordingly, the inner container 12 be described as being secured within the outer container 16 in a "fixed position," which shall refer broadly to the containers being in a linearly axially fixed relationship, even though they may be rotatable relative to the cap 20 and to each other into some other axial position. The cap 20 preferably includes a cavity 65 for receiving an identifying plug 66 (shown in phantom line in FIG. 2) therein, such as a color-coded plug member which can be wedged into a secure, seated position within the cavity 65.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A vial comprising:

a hollow inner container having an outer side and an open end and being configured for receiving a biological sample therein through the open end, said hollow inner container defining a first volume therein;

a hollow outer container having an open end and being configured for receiving the inner container therein;

one-piece unitary interconnecting means removably attachable to both the inner and outer container for (i) removably securing the inner container within the outer container in a fixed position such that the containers reside in a spaced-apart, substantially noncontacting orientation along the outer side of said inner container to thereby define a surrounding volume between said inner and outer containers which surrounds at least a portion of the inner container, and (ii) substantially closing off the open ends of the inner and outer containers from communication with surrounding environment of the vial such that the inner container is also substantially closed off from communication with the surrounding volume;

wherein the surrounding volume defined between the inner and outer containers is less than the first volume defined within the inner container;

wherein the inner and outer containers are tubular, said inner container having threads formed upon an outer surface thereof and said outer container having threads formed upon an inner surface thereof, and wherein the one-piece unitary interconnecting means comprises a cap member having a tubular wall of single wall construction extending outwardly from a continuous capping surface to a terminal rim of said tubular wall, said tubular wall including an inner surface having threads which are screwably engageable with the threads of the inner container and an opposing outer surface having threads which are screwably engageable with the threads of the outer container, wherein the cap member is configured and dimensioned to be simultaneously positioned over the open ends of the inner and outer containers with the tubular wall disposed in simultaneous threaded engagement with said inner and outer containers such that the capping surface and the tubular wall cooperatively close off the open ends of the containers.

2. A vial as defined in claim 1, wherein the containers and the cap member cooperatively define a substantially closed tortuous path between the surrounding environment of the vial and the open end of the inner container, said tortuous path extending from said surrounding environment into the open end of the outer container and along the threaded engagement between the outer container and the tubular wall of the cap member, into the surrounding volume and around the terminal rim of the tubular wall of the cap member, along the threaded engagement between the tubular wall of the cap member and the inner container, around the open end of the inner container and thereinto.

3. A vial as defined in claim 1, wherein the open end of the outer container is advanceable toward the capping surface when the tubular wall of the cap member is being screwed onto the outer container and wherein the open end of the inner container is also advanceable toward the capping surface when the tubular wall of the cap member is being screwed onto the inner container, said vial further comprising:

inner sealing means for establishing an inner seal between the open end of the inner container and the cap member to thereby seal the inner container.

4. A vial as defined in claim 3, further comprising:

outer sealing means for establishing an outer seal between the open end of the outer container and the cap member to thereby seal the surrounding volume from communication with the surrounding environment of the vial.

5. The vial of claim 1, wherein a ratio of the surrounding volume to the first volume is less than 0.5.

6. A vial comprising:

a hollow inner container having an open end and being configured for receiving a biological sample therein through the open end;

a hollow outer container having an open end and being configured for receiving the inner container therein;

one-piece unitary interconnecting means removably attachable to both the inner and outer container for (i) removably securing the inner container within the outer container in a fixed position such that the containers define a surrounding volume therebetween which surrounds at least a portion of the inner container, and (ii) substantially closing off the open ends of the inner and outer containers from communication with surrounding environment of the vial such that the inner container is also substantially closed off from communication with the surrounding volume;

said interconnecting means comprising a capping surface and a single tubular wall extending outwardly from said capping surface, said single tubular wall being configured for inserting between the inner and outer containers, wherein the inner container, outer container and single tubular wall are configured and dimensioned such that said single tubular wall resides sandwiched between, and in contact with, said inner and outer containers;

wherein the inner container, outer container and single tubular wall define a triple overlap section along a length portion of the tubular wall, said tubular wall residing contactably sandwiched between the inner and outer containers, and wherein the inner container, outer container and single tubular wall each define a wall thickness, the wall thickness of the single tubular wall at any overlap portion of the triple overlap section being less than the sum of the wall thicknesses of the inner and outer containers at said overlap portion.

7. The vial of claim 6, wherein the inner container includes threads formed upon an outer surface thereof and wherein the outer container includes threads formed upon an inner surface thereof, and wherein the single tubular wall of the interconnecting means includes interior threads configured for engaging with the threads of the inner container and exterior threads configured for engaging with the threads of the outer container.

8. A vial comprising:
  a hollow inner container having an open end and being configured for receiving a sample therein through the open end;
  a hollow outer container having an open end and being configured for receiving the inner container therein; and
  one-piece unitary interconnecting means removably attachable to both the inner and outer container for
    (i) removably securing the inner container within the outer container in a fixed position such that the containers define a surrounding volume therebetween which surrounds at least a portion of the inner container, and
    (ii) substantially closing off the open ends of the inner and outer containers from communication with surrounding environment of the vial such that the inner container is also substantially closed off from communication with the surrounding volume;
  wherein the inner and outer containers are tubular, said inner container having threads formed upon an outer surface thereof and said outer container having threads formed upon an inner surface thereof, and wherein the one-piece unitary interconnecting means comprises a cap member having a tubular wall extending outwardly from a continuous capping surface to a terminal rim of said tubular wall, said tubular wall including an inner surface having threads which are screwably engageable with the threads of the inner container and an opposing outer surface having threads which are screwably engageable with the threads of the outer container, wherein the cap member is configured and dimensioned to be simultaneously positioned over the open ends of the inner and outer containers with the tubular wall disposed in simultaneous threaded engagement with said inner and outer containers such that the capping surface and the tubular wall cooperatively close off the open ends of the containers;
  wherein the open end of the outer container is advanceable toward the capping surface when the tubular wall of the cap member is being screwed onto the outer container and wherein the open end of the inner container is also advanceable toward the capping surface when the tubular wall of the cap member is being screwed onto the inner container, said vial further comprising:
    inner sealing means for establishing an inner seal between the open end of the inner container and the cap member to thereby seal the inner container;
    wherein the inner sealing means comprises an annular rib extending outwardly from the capping surface in concentric, substantially co-axial orientation with the tubular wall of the cap member to thereby define an annular channel between said rib and said wall, such that when the cap member is screwed onto the inner container to advance the open end of the inner container toward the capping surface, said open end becomes sealably engaged within said annular channel.

9. A vial as defined in claim 8, wherein the inner container comprises a terminal rim defining the open end thereof, the inner sealing means further comprising the annular channel and the terminal rim being cooperatively configured and dimensioned to establish sealing bi-compression of the terminal rim between the annular rib and the tubular wall of the cap member when said cap member is screwed onto the inner container to advance the open end of the inner container toward the capping surface.

10. A vial as defined in claim 8, wherein the inner container comprises a terminal rim defining the open end thereof, the inner sealing means further comprising the annular channel and the terminal rim being cooperatively configured and dimensioned to establish sealing tri-compression of the terminal rim against the capping surface, the annular rib and the tubular wall of the cap member when said cap member is screwed onto the inner container to advance the open end of the inner container toward the capping surface.

11. A vial comprising:
  a hollow inner container having an open end and being configured for receiving a sample therein through the open end;
  a hollow outer container having an open end and being configured for receiving the inner container therein; and
  one-piece unitary interconnecting means removably attachable to both the inner and outer container for
    (i) removably securing the inner container within the outer container in a fixed position such that the containers define a surrounding volume therebetween which surrounds at least a portion of the inner container, and
    (ii) substantially closing off the open ends of the inner and outer containers from communication with surrounding environment of the vial such that the inner container is also substantially closed off from communication with the surrounding volume;
  wherein the inner and outer containers are tubular, said inner container having threads formed upon an outer surface thereof and said outer container having threads formed upon an inner surface thereof, and wherein the one-piece unitary interconnecting means comprises a cap member having a tubular wall extending outwardly from a continuous capping surface to a terminal rim of said tubular wall, said tubular wall including an inner surface having threads which are screwably engageable with the threads of the inner container and an opposing outer surface having threads which are screwably engageable with the threads of the outer container, wherein the cap member is configured and dimensioned to be simultaneously positioned over the open ends of the inner and outer containers with the tubular wall disposed in simultaneous threaded engagement with said inner and outer containers such that the capping surface and the tubular wall cooperatively close off the open ends of the containers;
  wherein the open end of the outer container is advanceable toward the capping surface when the tubular wall of the cap member is being screwed onto the outer container and wherein the open end of the inner container is also advanceable toward the capping surface when the tubular wall of the cap member is being screwed onto the inner container, said vial further comprising:
    inner sealing means for establishing an inner seal between the open end of the inner container and the cap member to thereby seal the inner container;
    outer sealing means for establishing an outer seal between the open end of the outer container and the cap member to thereby seal the surrounding volume from communication with the surrounding environment of the vial, wherein the outer sealing means comprises a resilient ring configured for placement between the open end of the outer container and the cap member so as to circumscribe the tubular wall of the cap member, such that when the cap member is screwed onto the outer container to advance the open end of the outer container toward the capping surface, the resilient ring becomes sealably sandwiched between said open end of the outer container and said cap member.

12. A vial comprising:

a hollow inner container having an open end and being configured for receiving a sample therein through the open end;

a hollow outer container having an open end and being configured for receiving the inner container therein; and one-piece unitary interconnecting means removably attachable to both the inner and outer container for
  (i) removably securing the inner container within the outer container in a fixed position such that the containers define a surrounding volume therebetween which surrounds at least a portion of the inner container, and
  (ii) substantially closing off the open ends of the inner and outer containers from communication with surrounding environment of the vial such that the inner container is also substantially closed off from communication with the surrounding volume;

wherein the inner and outer containers are tubular, said inner container having threads formed upon an outer surface thereof and said outer container having threads formed upon an inner surface thereof, and wherein the one-piece unitary interconnecting means comprises a cap member having a tubular wall extending outwardly from a continuous capping surface to a terminal rim of said tubular wall, said tubular wall including an inner surface having threads which are screwably engageable with the threads of the inner container and an opposing outer surface having threads which are screwably engageable with the threads of the outer container, wherein the cap member is configured and dimensioned to be simultaneously positioned over the open ends of the inner and outer containers with the tubular wall disposed in simultaneous threaded engagement with said inner and outer containers such that the capping surface and the tubular wall cooperatively close off the open ends of the containers;

a resilient sealing ring disposed around the inner surface of the outer container so as to extend radially inward therefrom, said sealing ring being engageable against the tubular wall of the cap member when said tubular wall is screwed into the outer container in threaded engagement therewith to thereby establish a seal between said outer container and said tubular wall of the cap member.

13. A vial comprising:

a hollow inner container having an open end and being configured for receiving a sample therein through the open end;

a hollow outer container having an open end and being configured for receiving the inner container therein; and one-piece unitary interconnecting means removably attachable to both the inner and outer container for
  (i) removably securing the inner container within the outer container in a fixed position such that the containers define a surrounding volume therebetween which surrounds at least a portion of the inner container, and
  (ii) substantially closing off the open ends of the inner and outer containers from communication with surrounding environment of the vial such that the inner container is also substantially closed off from communication with the surrounding volume;

wherein the inner and outer containers are tubular, said inner container having threads formed upon an outer surface thereof and said outer container having threads formed upon an inner surface thereof, and wherein the one-piece unitary interconnecting means comprises a cap member having a tubular wall extending outwardly from a continuous capping surface to a terminal rim of said tubular wall, said tubular wall including an inner surface having threads which are screwably engageable with the threads of the inner container and an opposing outer surface having threads which are screwably engageable with the threads of the outer container, wherein the cap member is configured and dimensioned to be simultaneously positioned over the open ends of the inner and outer containers with the tubular wall disposed in simultaneous threaded engagement with said inner and outer containers such that the capping surface and the tubular wall cooperatively close off the open ends of the containers;

wherein the inner container comprises a terminal rim defining the open end thereof, said vial further comprising an inner sealing means which comprises:
  a resilient sealing ring configured for placement between the capping surface and the terminal rim of the inner container such that when the cap member is screwed onto the inner container to advance the open end of the inner container toward the capping surface, the resilient ring becomes sealably sandwiched between said terminal rim of the inner container and said capping surface.

* * * * *